(12) United States Patent
Otterstedt

(10) Patent No.: US 9,108,854 B2
(45) Date of Patent: Aug. 18, 2015

(54) BIOCIDAL COLLOIDAL DISPERSIONS OF SILICA PARTICLES WITH SILVER IONS ADSORBED THEREON

(75) Inventor: Jan-Erik Otterstedt, Simrishamn (SE)

(73) Assignee: PREBONA AB, Lund (SE)

( * ) Notice: Subject to any disclaimer, the term of this patent is extended or adjusted under 35 U.S.C. 154(b) by 0 days.

(21) Appl. No.: 13/497,503

(22) PCT Filed: Sep. 20, 2010

(86) PCT No.: PCT/SE2010/051007
§ 371 (c)(1),
(2), (4) Date: Mar. 21, 2012

(87) PCT Pub. No.: WO2011/037523
PCT Pub. Date: Mar. 31, 2011

(65) Prior Publication Data
US 2012/0301553 A1 Nov. 29, 2012

(30) Foreign Application Priority Data

Sep. 22, 2009 (SE) ...................................... 0901216

(51) Int. Cl.
*A01N 25/08* (2006.01)
*A01P 15/00* (2006.01)
(Continued)

(52) U.S. Cl.
CPC ............... *C01B 33/14* (2013.01); *A01N 25/08* (2013.01); *A01N 59/16* (2013.01); *B82Y 30/00* (2013.01); *C01B 33/149* (2013.01); *C01B 33/1417* (2013.01); *C01B 33/18* (2013.01);
(Continued)

(58) Field of Classification Search
None
See application file for complete search history.

(56) References Cited

U.S. PATENT DOCUMENTS 4,284,580 A * 8/1981 Logan et al. .................. 554/193
5,510,109 A   4/1996 Tomioka et al.
(Continued)

FOREIGN PATENT DOCUMENTS

CN    1623898    6/2005
EP    0488269    6/1992
(Continued)

OTHER PUBLICATIONS

Flores, et al. "Preparation of core—shell nanospheres of silica—silver: SiO2@Ag", Journal of Non-Crystalline Solides, Oct. 2008, 5435-5439.*
(Continued)

*Primary Examiner* — Ernst V Arnold
*Assistant Examiner* — Jianfeng Song
(74) *Attorney, Agent, or Firm* — Brooks Kushman P.C.

(57) ABSTRACT

A colloidal dispersion having carrier particles of silica having a particle size from 3 nm to 100 nm to which silver ions have been adsorbed, preferably in an amount of 0.0005-5 silver ions per nm2 of silica particle surface. The surface of the carrier particles of silica suitably contains aluminumsilicate sites. It also relates to a process for making a colloidal dispersion comprising providing a silica sol, adding a solution of silver nitrate to the silica sol under agitation yielding a colloidal dispersion with silver ions adsorbed on the surface of the silica particles. The dispersion is usable as a biocide in e.g. coatings, adhesives and sealants, in surface treatment and impregnation of organic materials, in surface treatment and impregnation of inorganic materials, in textiles, garments and shoes, in medical disposables, in plastics and rubbers, in water and air purification, and in crop protection.

11 Claims, 2 Drawing Sheets

Figure 1:
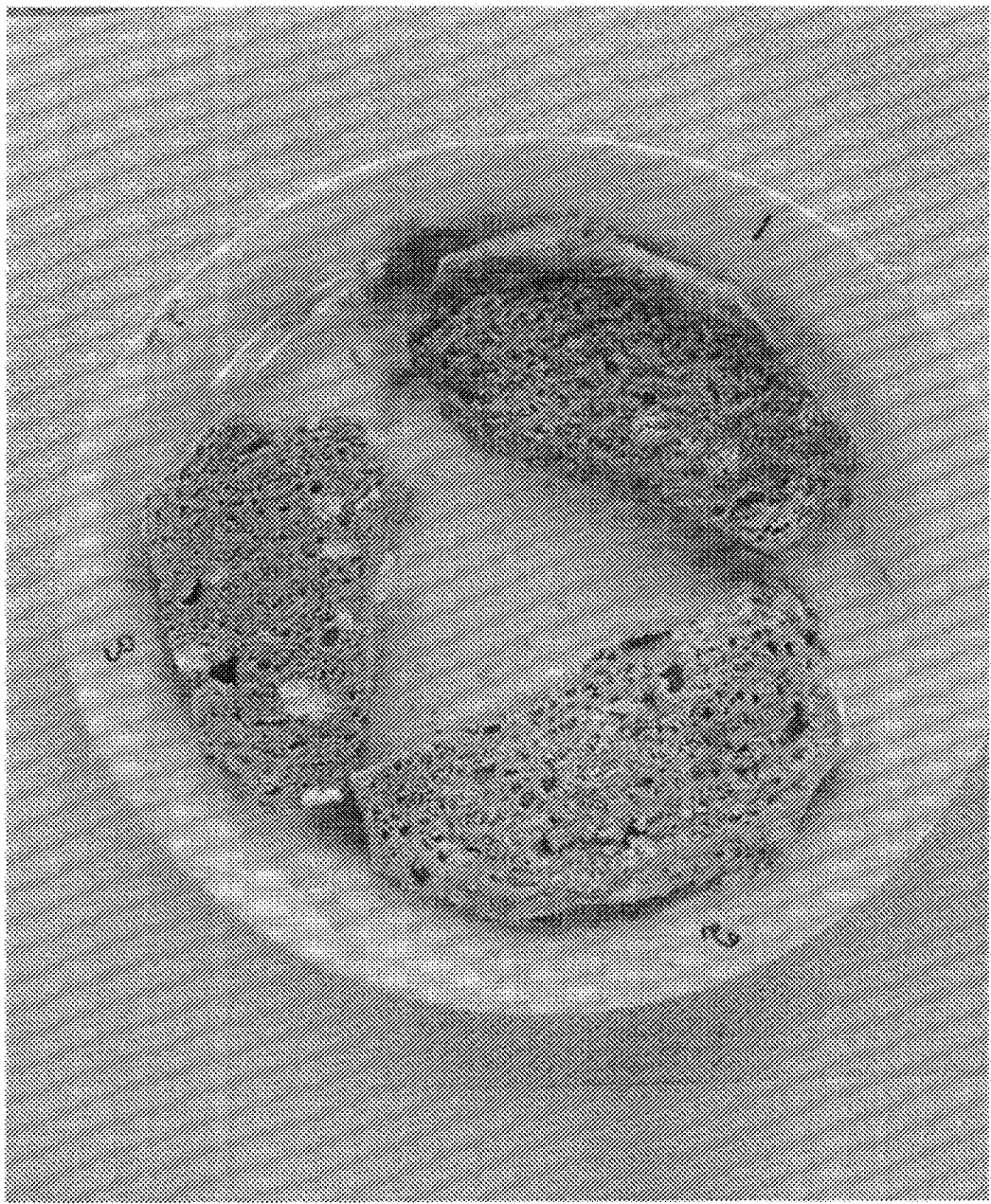

(51) Int. Cl.

| | | |
|---|---|---|
| *A01N 59/16* | (2006.01) | |
| *C01B 33/14* | (2006.01) | |
| *B82Y 30/00* | (2011.01) | |
| *C01B 33/141* | (2006.01) | |
| *C01B 33/149* | (2006.01) | |
| *C01B 33/18* | (2006.01) | |
| *C01G 5/00* | (2006.01) | |
| *C09C 1/30* | (2006.01) | |
| *C09D 5/14* | (2006.01) | |
| *C09D 7/12* | (2006.01) | |
| *C08K 3/36* | (2006.01) | |
| *C08K 9/02* | (2006.01) | |

(52) U.S. Cl.
CPC ............... *C01G 5/00* (2013.01); *C09C 1/3045* (2013.01); *C09D 5/14* (2013.01); *C09D 7/1225* (2013.01); *C09D 7/1266* (2013.01); *C09D 7/1275* (2013.01); *C01P 2004/64* (2013.01); *C01P 2006/12* (2013.01); *C01P 2006/80* (2013.01); *C08K 3/36* (2013.01); *C08K 9/02* (2013.01)

(56) References Cited

U.S. PATENT DOCUMENTS

| | | | |
|---|---|---|---|
| 5,651,978 | A | 7/1997 | Tomioka et al. |
| 5,730,995 | A | 3/1998 | Shirono et al. |
| 7,511,007 | B2 | 3/2009 | Tichy et al. |
| 8,048,193 | B2 | 11/2011 | Taniuchi et al. |
| 8,191,169 | B2 | 6/2012 | Grune et al. |
| 8,450,235 | B2 | 5/2013 | Suzuki et al. |
| 2005/0084632 | A1* | 4/2005 | Urlaub et al. ............. 428/34.1 |
| 2007/0009672 | A1 | 1/2007 | Jeong et al. |
| 2007/0190174 | A1 | 8/2007 | Holladay et al. |
| 2009/0013825 | A1 | 1/2009 | Rahman Nia |
| 2010/0150980 | A1 | 6/2010 | Bokorny et al. |
| 2010/0266990 | A1 | 10/2010 | Cooley et al. |

FOREIGN PATENT DOCUMENTS

| | | |
|---|---|---|
| EP | 2018839 | 1/2009 |
| EP | 2027956 | 2/2009 |
| KR | 2005120295 | * 12/2005 |
| WO | 2004073400 | 9/2004 |
| WO | 2006128793 | 12/2006 |
| WO | 2007117087 | 10/2007 |
| WO | 2008024422 | 2/2008 |
| WO | 2008024426 | 2/2008 |
| WO | 2008033206 | 3/2008 |
| WO | 2008079149 | 7/2008 |
| WO | 2008110163 | 9/2008 |
| WO | 2008122131 | 10/2008 |
| WO | 2008147395 | 12/2008 |
| WO | 2008147427 | 12/2008 |
| WO | 2009036714 | 3/2009 |
| WO | 2009054462 | 4/2009 |

OTHER PUBLICATIONS

Matijevic et al. "Stability of Colloidal Silica", Journal of Colloid and Interface Science, vol. 35, Apr. 1971, 560-568.*
English Abstract of KR2005120295, Dec. 2005.*
International Search Report for PCT/SE2010/051007, Completed by the Swedish Patent Office on Jan. 12, 2011, 4 Pages.
Translation of Chinese Office Action for Application No. CN 201080042069.0, Issue Date of Aug. 9, 2013, 7 Pages.

* cited by examiner

US 9,108,854 B2

BIOCIDAL COLLOIDAL DISPERSIONS OF SILICA PARTICLES WITH SILVER IONS ADSORBED THEREON

CROSS-REFERENCE TO RELATED APPLICATION

This application is the U.S. national phase of PCT Appln. No. PCT/SE2010/051007 filed Sep. 20, 2010, which claims priority to Swedish application 0901216-2 filed on Sep. 22, 2009, the disclosures of which are incorporated in their entirety by reference herein.

FIELD OF THE INVENTION

Present invention relates to colloidal nano-composites of silver. In particular it relates to such materials consisting of nano particles, for instance colloids, having a well controlled size and a high degree of dispersion of silver. It also relates to processes for making such materials and using them in different applications where a biocidal effect is desired.

BACKGROUND AND PRIOR ART

Nanotechnologies are the science and business of manipulating matter at the atomic scale. Materials produced with the aid of various kinds of nanotechnologies are starting to be used in many areas of everyday life such as cosmetics, clothing fabrics, sports equipment, paints, packaging, food, etc. and has been used for some time as for instance catalysts in many important industrial processes. In the future we will no doubt see many more application of nanomaterials in general and of nanomaterials involving noble metals in particular.

Colloidal gold has been successfully used as a therapy for rheumatoid arthritis. An in vitro experiment has shown that the combination of microwave radiation and colloidal gold can destroy the beta-amyloid fibrils and plaque which are associated with Alzheimer's disease. Gold nanoparticles are being investigated as carriers for drugs such as Paclitaxel. In cancer research, colloidal gold can be used to target tumors and provide detection using SERS, Surface Enhanced Raman Spectroscopy in vivo.

Samsung home appliances, such as refrigerators or air conditioners, come with a silver nano coating to their inner surfaces which provide an overall anti-bacterial and anti-fungal effect. As air circulates, the coated surfaces contact with the silver ions which can resist any airborne bacteria, which in turn suppress the respiration of bacteria, adversely affects bacteria's cellular metabolism and inhibits cell growth. Samsung maintain that the silver nano technology sterilizes over 650 types of bacteria and a "Samsung WM1245A Washing Machine releases over 400 billion silver ions which penetrate deeply into fabrics of any kind and create a coat of sterilizing protection for a maximum of 99.99% disinfection and an added antibacterial effect of up to 30 days after washing".

There is an effort to incorporate silver nanoparticles, which have an antimicrobial effect that lasts longer than ionic silver, into a wide range of medical devices, including but not limited to bone cement, surgical instruments, surgical masks, wound dressings.

WO 2008/079149 A1 describes an antimicrobial formulation for dental applications that includes colloidal silver, from between about 0.01 to 2%, and colloidal copper, from between about 0.05 to 10%.

WO 2008/147395 A2 claims a solid or a foamed rubber, synthetic rubber, or neoprene, or other suitable polymer compound containing nanoparticles of at least one metal or metal compound comprising silver, gold, palladium, platinum and copper.

WO 2008/024422 A2 discloses incorporation of colloidal silver in compositions for use in partially or fully decontaminating surfaces which have been contaminated with chemical or biological warfare agents as well as to methods for treating viral infections, bacterial infections, fungal infections, and cancerous tissue.

WO 2008/033206 A1 is drawn to disinfectant compositions, which are human safe, that is food grade or food safe that may contain colloidal silver.

EP 2 018 839 A1 discloses preservative compositions with 0.1 to 1 ppm electrolytic silver for cosmetic products.

US 2009/0013825 A1 to provide a simple preparation method for silver nano particles having a well-controlled size in a surfactant solution. The nano silver colloid is prepared by the following step-wise procedure: (1) dissolving silver nitrate crystal in distilled water; (2) adding surfactant, LABS (Linear alkyl benzene sulfonate) to the solution and; (3) adding reducing agent to the solution. The preferred reducing agent is hydrazine.

US 2007/0009672 A1 describes a method for preparation of nanocomposite solution, comprising preparing basic silica colloid aqueous solution; providing an electrolysis apparatus by installing a negative electrode containing aluminum and a positive electrode containing silver into the basic silica colloid aqueous solution; and forming nanocomposite by applying voltage to the respective electrodes of the electrolysis apparatus. With this configuration, the present invention provides a method of manufacturing solution dispersed with nanocomposite, further particularly to, a method of manufacturing nanocomposite solution having excellent storability and thermal stability and containing silver having antibacterial function, WO 2007/117087 A1 is drawn to provide a facilitated olefin transporting polymer membrane, which is capable of separating olefin and paraffin from each other using metal nanoparticles, in particular, silver nanoparticles, gold nanoparticles, or copper nanoparticles, as a carrier for facilitated transport.

WO 2008/024426 A2 provides hygienic absorbent articles, such as feminine sanitary napkins, tampons and disposable diapers, having antimicrobial activity that can minimize odors caused by body fluids. The articles of the invention include an absorbent member such as an elongated absorbent portion or pad that contains an antibacterial amount of substantially immobilized nanosilver particles or particles containing silver ions, preferably encased in a granule of a soluble carrier such as dextran, and the like, or a water-insoluble, but water-swellable superabsorbent polymer.

WO 20081100163 relates to a method of manufacturing silver nanoparticles, cellulosic fibers and nanofibers containing silver nanoparticles, fibers and nanofibers containing silver nanoparticles, use of silver nanoparticles to the manufacture of cellulosic fibers and nanofibers, and wound dressing containing silver nanoparticles.

WO 2008/147427 A2 A colorless composition comprising silver particles and water is disclosed. The particles have an interior of elemental silver and an exterior of ionic silver oxide, wherein the silver particles are present in the water at a level of about 5-40 ppm A preferred embodiment of the invention is a silver composition comprising particles of silver wherein more than 50% of the particles are less than 0.015 micrometers in size and the particles are colloidally suspended in water.

The composition manifests significant antiviral properties and is effective against avian influenza virus. Methods of use of the composition are described.

WO 2009/036714 A1 discloses is a composition for the treatment of wounds, containing hyaluronic acid, urea, and colloidal silver.

EP 2 027 956 A1 relates to a method for producing gold colloid including a nucleation step of forming nuclear colloidal particles by adding a first reducing agent to a first gold salt solution; and a growth step of growing nuclear colloid by adding a second gold salt and a second reducing agent to the solution of the nuclear colloidal particles, characterized in that the growth step is performed at least once; a citrate is used as the first reducing agent and an ascorbate is used as the second reducing agent; and the addition of the ascorbate in the growth step is performed simultaneously with addition of the second gold salt.

Prior art describes the preparation and use of colloidal forms of noble metals, in particular colloidal silver, as biocides in various applications. Particle size and particle size distribution are often described as important properties of such colloidal dispersions although their values are rarely specified. In some prior art it is stated that it is desirable that at least 50% of the particle sizes have a particle size smaller than 15 nanometers. When nano-particles of noble metals are used as biocides only the metal atoms at the surface of the particles are able to come into contact with and interact with microbes of different kinds. Metal atoms in the interior of the particles have no access to the environment outside of the particles and therefore have no biocidal activity. Let $n_s$ and $n_t$ denote the number of surface atoms and the total number of atoms, for instance noble metal atoms, respectively. The ratio $n_s/n_t$ is called the degree of dispersion of the noble metal and is a very important property of noble metals in applications, for instance many catalytic applications or biocidal applications, where their performance depend on the number of atoms they expose to their environment. The degree of dispersion decreases rapidly with particle size. In the case of for instance nano-particles of silver, the degree of dispersion thus decreases from about 85% to about 30% when the particle size grows from 1 nanometer to 5 nanometers. The degree of dispersion of 15 nanometer particles is less than 10%, indicating that more than 90% of the metal resides inactive in the interior of the particles.

Prior art also describes the use of ions of noble metals as biocides. One might say that the ions of for instance silver salts in aqueous solutions are perfectly dispersed; in such solutions the degree of dispersion of the noble metals is 100% as it were, but they may also be removed, for instance by leaching, from places where their biocidal function is needed and end up in places where their biocidal function is unwanted.

SUMMARY OF THE INVENTION

It is well known that silver has biocidal properties but there is need for a new form of silver that combines high biocidal activity with the excellent non-leachability of nano-particles and the perfect dispersion of ions. This means that a given effect can be achieved with much less silver in the form of the material of the present invention than with silver in conventional colloidal dispersions.

It is therefore an object of the present invention to provide forms of silver that are colloidal in nature, i.e. is they consist of nano-sized particle, yet display a virtually perfect dispersion of the metal species. In one embodiment of the invention, silver ions are adsorbed on the surface of the particles of colloidal dispersions of silica.

Another aspect of the present invention is that colloids with significantly higher concentrations of silver can be achieved than is possible in conventional colloidal dispersions of silver. A further aspect of the invention is that particle size and particle size distribution can be tailor made to meet narrow specifications. Another aspect of the present invention is that the relatively high concentrations of silver that can be obtained facilitate formulations of many products, for instance paints and sealants, containing materials of the present invention.

Another aspect is that the process for making materials of the present invention is simple, robust and cost effective.

It is well known that if pH of a silver salt solution is raised to above 8 or 9 silver oxide, $Ag_2O$, is precipitated. It is therefore surprising that silver can exist in relatively high concentrations, for instance 1000 to 2000 ppm silver, in the materials of this invention, many of whom have pH higher than 9, without precipitating.

Moreover, it is well known that if soluble chlorides, for instance in the form of a solution of sodium chloride, is added to a solution of silver nitrate a white precipitate of silver chloride will form immediately. If, on the other hand, a solution of sodium chloride under similar conditions is added to a material of the present invention no precipitation will form.

BRIEF DESCRIPTION OF THE FIGURES

FIG. 1 shows three slices of bread after 3 days in the warm and humid atmosphere; and FIG. 2 shows the effect of the invention on roof tiles covered with green moss.

DETAILED DESCRIPTION OF THE INVENTION

Silica

A convenient source of the silica particles of the present invention are commercial silica sols. Such sols are aqueous dispersions of silica particles and the particles are uniform spheres of silica, which have no internal surface area or detectable crystallinity. They are usually dispersed in an alkaline medium, which reacts with the silica surface to produce a negative charge. Because of the negative charge, the particles repel one another resulting in a stable product.

In some commercial products, the particle surface is modified with aluminosilicate ions so as to provide the surface with a fixed, pH-independent negative charge that will make the products more stable towards gelling than the sols from which they were prepared. Trivalent aluminium atoms have been substituted for part of the tetravalent silicon atoms in the surface of the particles, creating a fixed negative charge which is independent of pH. The surface coverage of Al is much less than that corresponding to a Langmuir monolayer.

There are also commercial silica sols in which the particles have a positive charge and are dispersed in an acidic solution. The negative surface charge has been reversed by adsorption of octahedral aluminium ions such as those present in basic aluminium chloride. The solids content depends on the particle size and varies from less than 10% per weight silica for the smallest particles, 3 nm, to about 50% per weight silica for larger particles, >20 nm. The surface of the particles in aqueous silica sols is covered with surface hydroxyl groups, silanol groups. The particle size of the silica sols used as carrier of the present invention is typically in the range of 3-250, preferable, 4-100 nm, more preferable 5-25 nm, even more preferable 6-15 nm and most preferable 7-10 nm, corresponding to a specific surface area (e.g. by SEARS's titration or BET) to typically 20-1000 $m^2/g$, preferable 30-750 $m^2/g$, more preferable to 100-500 $m^2/g$, even more preferable to 200-400 $m^2/g$, and most preferable 250-370 $m^2/g$.

Stabilization of commercial silica sols is accomplished by adjusting the pH of the sol to between 8.0 and 10.0 by addition of alkali, usually a solution of sodium hydroxide. The sols also contain small amounts of other electrolytes such as sodium chloride and sodium sulfate.

The stability of highly concentrated silica sols is very sensitive to the presence of electrolytes. The electrolyte concentration can be reduced to a minimum by using ion exchange resins. The silica sols used to prepare the materials of the present invention are commercial products or commercial silica sols modified, for instance by treating the sols with sodium aluminate solution so as to create aluminosilicate sites on the particle surface in order to obtain a silica sol that is stable in the pH range of 4-11, by methods well known in the trade. The particles of the silica sols used to prepare the materials of the present invention carry an anionic charge and the sols are anionic sols.

Stability

The term stable used in the present invention means that the product should be stable toward gelling, implying that the relative viscosity should not increase more than 100% (e.g. from 5 to 10 mPas) under a period of about two months. The term also means stability toward precipitation; that is there is no substantial precipitation of solid content, mainly silver species, characterised by that no more than 20% of the solid material has precipitated and settled as a sludge on the bottom, if stored properly (i.e. no light and otherwise correct storage conditions), for a period of two months.

Procedures and Methods

Nano-composite materials according to the present invention are prepared by contacting a non-metallic carrier material in the form of e.g. colloidal silica with a solution comprising silver ions. The reactants and products used in the various preparations and methods fall in the domain of colloids and colloid chemistry and due care has to be taken concerning concentration of reactants and products, maintaining a high electrical charge on colloidal particles, using water of good quality, preferably deionised water, observing proper rate of addition and order of addition of the components, working in conservative but realistic temperature ranges and providing sufficient agitation and stirring so as to maintain stability towards gelling or aggregation of reactants and products.

Concentrations of colloidal silica used in the various preparations of the present invention vary from one weight % $SiO_2$ or less to undiluted commercial sols that could contain 30 weight % $SiO_2$ or more.

Most soluble silver salts can be used to prepare the materials of the present invention but the preferred salt is silver nitrate.

The concentration of the silver salt solutions used in the various preparations is preferable in the range of 0.01M-1.0 M more preferable 0.03 M-0.5 M, most preferable about 0.05-0.4 M. Most of the time 0.1 molar solutions have been used but higher, for instance 1 molar $AgNO_3$ and 0.5 molar $AgNO_3$, or lower concentration have also been used.

The charge of metal ions in solution, usually aqueous solutions, is normally positive. This is the case for silver, which usually, but not always, forms monovalent cations in aqueous solutions.

So as to achieve strong adsorption of metal ions on the surface of nano-sized carrier particles the electrical charge of the latter should be high but of opposite charge to that of the metal ions.

The charge on the particles in colloidal silica or the particles of silica in an aqueous environment increases exponentially with pH and is almost 0.5 units of negative charge per $nm^2$ particle surface at pH of about 10 and at very low, $10^{-4}$ normal, electrolyte concentrations. Colloidal silica has a local stability maximum at the point of zero charge, which occurs at about pH 2.0. The stability of a silica sol first decreases with pH and reaches a minimum around pH 6, after which the sol enters a region of high stability between pH 8 and pH 10.5.

The surface charge of silica, and of many other metal oxides as well, can be altered by modifying the surface in different ways. In one method, when the particle surface of silica sols is modified with aluminosilicate ions, the surface will have a fixed, pH-independent negative charge that will make the sol more stable towards gelling by the presence of electrolytes and at low pH, for instance pH 4-5, than the sols from which they were prepared.

A convenient way to introduce aluminosilicate sites on the surface of colloidal silica is to use weak acid cation resin to remove sodium ions from the silica sol-sodium aluminate system and thus bring about reaction of the aluminate ions with the silica surface. In this system, pH will usually not fall below pH 5 even if an excess of weak acid cation exchange resin is used.

A calculated amount of sodium aluminate solution to give the desired number of aluminosilicate sites per $nm^2$ particle surface is simply added to the slurry of colloidal silica and resin.

The creation of aluminosilicate sites on the surface of silica is well described in the literature, (e.g. in Iler, The Chemistry of Silica, 1979, pp. 407-409). Such descriptions also indicate that it is difficult to introduce much more than about 2 aluminosilicate sites per $nm^2$ silica surface, for example The concentration of aluminosilicate sites on the surface of the ultimate particles making up the materials of this invention falls in the range from about 0.20-2.0 site per $nm^2$, more preferable, 0.50-1.50, even more preferable, 0.70-1.25.

The aluminosilicate sites carry a negative charge, which must be neutralized by counter ions, most often $Na^+$ ions. Modification of the silica surface with sodium aluminate converts the surface to a cation exchanger.

Although adsorption of metal cations on aluminosilicate-modified silica sols can be carried out over a wide pH range it is preferable to carry out the adsorption in the pH range where silica sols are most stable; that is the alkaline range, for instance in the pH range from about 8 to about 10.5.

The rate at which silver salt solution can be added to the silica sol without destabilizing the sol depends on the conditions being used in the preparation. The rate of addition can be fast as long as the increments of added salt are virtually instantaneously dispersed throughout the sol and there rapidly adsorbed onto the silica particles. It is actually quite surprising how robust the colloidal systems, prepared by the technology of the present invention, are. In many of the small scale preparations it is actually possible to inject 0.1 m $AgNO_3$ solution into magnetically stirred silics sols in very short times, for instance 10-15 seconds, without destabilizing the sols. However, in most of the small scale laboratory preparations, for instance preparations of sols containing about 500 ppm of metal, longer addition times of 0.1 molar silver salt solutions, typically 2-3 minutes were used so as to be on the safe side in terms of having good stability towards gelling or aggregation. Sols with higher silver contents may require longer times of addition. Thus, a sol containing 1500 ppm silver may require a time of addition of 0.1 molar silver solutions of about 12 minutes. Similar time scales will apply to larger scale preparations provided that agitation or stirring is as efficient as in the small scale preparations.

A sol of a given concentration of silver can be prepared in different ways. In one method, a certain amount of silver nitrate solution is added to a silica sol with specified values of particle size and concentration of silica. In another method, the same amount of silver nitrate solution is added to a sol of the same particle size but higher, for instance four times higher, concentration of silica. The overall concentration of silver is the same in the two sols but the concentration of silver on the particle surface of the former sol is higher—four times higher—than that of the latter sol. Thus, a material of the present invention with a given, overall concentration of silver and a given particle size can be obtained by combining high concentration of particles, that is high concentration of silica, with low concentration of silver on the particle surfaces or by combining high surface concentration of silver with low silica concentration.

The concentrations of silica of the sols (product) of the present invention vary from less than 0.1% $SiO_2$ to 50% $SiO_2$ preferably 0.5-30% $SiO_2$, or more preferably 1-25% $SiO_2$ and most preferable 2-10% by weight of $SiO_2$, while the remaining part (adding up to 100%) comprising e.g. silver ions (species) and water.

The concentration of silver ions (species) on the surface of the ultimate particles making up the materials of this invention falls in the range from about 0.0005 (0.005) to more than 5 silver ions (species) per $nm^2$ preferable 0.20-2.0, more preferable 0.50-1.50, and even more preferable 0.70-1.25 ions (species) per $nm^2$. Typically one silver ion (species) adsorbs on one charged Al—Si-site but not all Al—Si sites may have adsorbed silver species adsorbed on them. The ratio by number between silver ions (species) and Al—Si sites may vary within 0.01-1.0 but is preferably between 0.05-0.8.

The invention will be better understood but not limited by reference to the following illustrative examples.

EXAMPLES

In examples 1 through 31 (given in Table 1 below), indicated amounts of 0.1 m silver nitrate solutions were added to 50 g of magnetically stirred silica sols in the times also indicated in the table. In examples 32-35 larger amounts of sol were made. In example 31 for instance, 1000 grams of starting sol was used. Columns 2 to 4 give the particle size, concentration of $SiO_2$ in the starting sol and the number of aluminosilicate sites per $nm^2$ particle surface, respectively. Columns 5 and 10 show pH of the sol before and after addition of silver salt solution. In the first 30 examples, save example 19, silver nitrate solution was added using a plastic pipette. In example 19 and examples 32-35, silver nitrate solution was added using a Watson pump.

Patent Examples

| Example | Particle size, nm | Silica concentr. % | Aluminosilicate sites per $nm^2$ | pH of starting sol | Amount of 0.1 m $AgNO_3$ solution, g | Time of addition, minutes | Concentr. of ads. metal in sol, ppm | pH of composite sol |
|---|---|---|---|---|---|---|---|---|
| 1 | 12 | 5 | 0 | 9.88 | 2.55 | 2.5 | 500 | 9.61 |
| 2 | 12 | 10 | 0 | 9.85 | 5.10 | 5 | 1000 | 9.55 |
| 3 | 12 | 15 | 0 | 9.85 | 7.60 | 8 | 1500 | 9.48 |
| 4 | 12 | 30 | 0 | 9.90 | 2.51 | 2.5 | 500 | 9.82 |
| 5 | 22 | 5 | 0 | 9.52 | 2.55 | 2.5 | 500 | 9.08 |
| 6 | 22 | 10 | 0 | 9.50 | 5.10 | 5 | 1000 | 8.91 |
| 7 | 22 | 15 | 0 | 9.45 | 7.60 | 8 | 1500 | 8.82 |
| 8 | 3 | 7 | 0.6 | 9.35 | 2.51 | 2.5 | 500 | 9.04 |
| 9 | 5 | 1 | 0.7 | 9.72 | 2.55 | 2.5 | 500 | 8.56 |
| 10 | 5 | 3 | 0.7 | 9.76 | 5.10 | 5 | 1000 | 8.67 |
| 11 | 5 | 5 | 0.7 | 9.79 | 2.48 | 2.5 | 500 | 9.34 |
| 12 | 5 | 15 | 0.7 | 10.02 | 2.54 | 2.5 | 500 | 9-68 |
| 13 | 7 | 5 | 1.0 | 10.61 | 2.55 | 2.5 | 500 | 9.77 |
| 14 | 7 | 10 | 1.0 | 10.12 | 2.55 | 2.5 | 500 | 9.76 |
| 15 | 7 | 15 | 1.0 | 10.02 | 2.54 | 2.5 | 500 | 9.68 |
| 16 | 7 | 10 | 1.0 | 10.61 | 5.10 | 5 | 1000 | 9.53 |
| 17 | 7 | 15 | 1.0 | 10.61 | 7.60 | 8 | 1500 | 9.34 |
| 18 | 12 | 15 | 1.6 | 11.35 | 15.2 | 12 | 2518 | 9.58 |
| 19 | 12 | 27.1 | 1.6 | 11.16 | 30.0 | 200 | 4080 | 9.59 |
| 20 | 12 | 10 | 1.6 | 10.81 | 5.10 | 0.1 | 1000 | 10.18 |
| 21 | 12 | 27.1 | 1.6 | 10.77 | 0.51 | 1 | 100 | 10.77 |
| 22 | 12 | 27.1 | 1.6 | 10.77 | 2.55 | 2.5 | 500 | 10.70 |
| 23 | 12 | 27.1 | 1.6 | 10.77 | 5.10 | 5 | 1000 | 10.64 |
| 24 | 22 | 5 | 0.7 | 9.22 | 2.55 | 2.5 | 500 | 8.81 |
| 25 | 22 | 10 | 0.7 | 9.43 | 5.10 | 2.5 | 1000 | 8.69 |
| 26 | 22 | 15 | 0.7 | 9.50 | 7.60 | 2.5 | 1500 | 8.65 |
| 27 | 22 | 5 | 1.5 | 10.61 | 2.55 | 2.5 | 500 | 9.97 |
| 28 | 22 | 10 | 1.5 | 10.61 | 5.10 | 5 | 1000 | 9.75 |
| 29 | 100 | 20 | 1.5 | 11.12 | 2.55 | 2.5 | 500 | 9.67 |
| 30 | 100 | 25 | 1.5 | 11.12 | 5.10 | 5 | 1000 | 9.52 |
| 31 | 5 | 4 | 0.7 | 9.80 | 5.56 | 3 | 1200 | 8.52 |
| 32 | 12 | 10 | 0.8 | 10.32 | 50.00 | 50 | 500 | 9.76 |
| 33 | 5 | 3 | 0.7 | 9.76 | 50.0 | 52 | 1000 | 8.65 |
| 34 | 12 | 3 | 1.6 | 10.87 | 15.3 | 20 | 1434 | 8.21 |
| 35 | 12 | 3 | 1.6 | 10.87 | 52.8 | 113 | 1616 | 8.61 |

Examples 36 and 37 show that silver nitrate solutions with high concentrations of silver can be used to prepare the materials of this invention.

Example 36

6.0 g 0.5 m $AgNO_3$ solution was added with a plastic pipette to 50 g of 12 nm silica sol with a degree of aluminization of 1.6 Al per $nm^2$ of particle surface and containing 15% by weight of $SiO_2$ in 7 minutes and with magnetic stirring. The Ag-content of the silver coated silica sol was 5785 ppm.

Example 37

0.7 g 1.0 m $AgNO_3$ solution was added with a plastic pipette to 50 g of 5 nm silica sol with a degree of aluminization of 0.7 Al per $nm^2$ of particle surface and containing 5% by weight of $SiO_2$ in 4 minutes and with magnetic stirring. The Ag-content of the silver coated silica sol was 1500 ppm.

The following example describes modification of the surface of silica particles by treating silica sols with sodium aluminate solutions.

Example 38

The pH of a 22 nm sol containing 20% $SiO_2$ was adjusted to 8.5 with a strong-acid cation exchange resin in the hydrogen form. A quantity of 2500 grams of this sol was placed in a beaker and 9.12 g of sodium aluminate solution (prepared by diluting 2.914 g $NaAlO_2$ in 6.205 g deionized water) was added dropwise to the vortex of the violently stirred silica sol over a period of about 25 minutes. The resulting sol had a pH of 9.5. Assuming that all the added aluminium formed aluminosilicate sites, there would be 0.3 such sites per $nm^2$ of silica surface. The procedure can be repeated and the number of aluminosilicate ions per nm2 can be increased to about 2 in steps of preferably 0.3 sites per repetition.

The next two examples shows the unique properties of the metals of the colloidal metal nanocomposites of the present invention.

Example 39

The sol of example 26 was diluted to 100 ppm Ag. O.1 m $AgNO_3$ solution was diluted to 100 ppm Ag.

To each of the solutions were added 5 drops of 0.1 m NaCl solution. A whitish precipitate was immediately formed in the $AgNO_3$ solution but the sol was unaffected by the addition of NaCl.

Example 40

The sol of example 32 looks like a water clear solution with a slightly darkish tint. The silver content is 1000 ppm and pH is 8.65. By comparison, when silver nitrate was added to water of pH 8.65 to give a solution also containing 1000 ppm silver a precipitate was formed immediately.

The following two examples show the biocidal effect of products of the present invention.

Example 41

The sol of example 28 and 0.1 m $AgNO_3$ solution diluted to 1000 ppm Ag were used in this example. Slices of French bread from a local baker were used as substrates for fungal growth.

1. Bread slice was brushed on all sides with the sol containing 1000 ppm Ag
2. Bread slice brushed on all sides with 0.1 m $AgNO_3$ solution diluted to 1000 ppm Ag
3. Bread slice was untreated.

The bread slices on a dinner plate were put in a plastic bag, which in turn was placed in a glassed-in porch where the temperature varied between 20 and 35° C. over the day.

FIG. 1 shows the slices of bread after 3 days in the warm and humid atmosphere.

The untreated bread slice (slice 3) is severely befouled and the slice seems to be completely invaded by fungi. Treatment with $AgNO_3$ solution (slice 2) affords some protection but this slice also seems to be overrun by fungi. While fungi has gained foothold in a few spots on the surface of the slice treated with the sol of the present invention (slice 1 in FIG. 1), this sample is relatively resistant to fungi attack.

Example 42

Figure 2:

The sol of example 20 was brushed onto a roof tile covered with green moss. Instantaneously, at the first contact with the sol, the moss turned black—see FIG. 2.

Example 43

The sol of example 25 was readily blended into commercial laquers and paints, for instance Nanofloor Refresher from Nanosol AB, Gothenburg, Sweden, and Alpina Lackfärg V, a matte, white outdoor paint with an acrylic binder, from Alpina AB, Gothenburg, Sweden, to give stable formulations containing 100 ppm silver.

The experiments show that the materials of this invention can be prepared as stable sols with silica contents in the range from less than 1% $SiO_2$ to more than 25%, concentration of silver species in the material from less than 5 ppm to more than 5 000 ppm Ag.

The materials of this invention are efficient biocides. They can be used as is or blended into commercial paints and laquer to give stable formulations with biocidal properties.

The invention claimed is:

1. A stable biocidal colloidal dispersion comprising carrier particles of silica having a particle size from 3 nm to 100 nm to which silver ions have been adsorbed in an amount of 0.0005-5 silver ions per $nm^2$ of silica particle surface, wherein the colloidal dispersion is stable towards gelling and precipitation and has a concentration of silver ions of 5 ppm to 10,000 ppm and the carrier particles and adsorbed silver ions provide biocidal activity.

2. The colloidal dispersion according to claim 1, to which silver ions have been adsorbed in the amount of 0.005-3 silver ions per $nm^2$ of silica particle surface.

3. The colloidal dispersion according to claim 1, wherein the surface of the carrier particles of silica contains aluminumsilicate sites.

4. The colloidal dispersion according to claim 1 where the surface of the carrier particles of silica contains 0.3-2 aluminumsilicate sites per $nm^2$.

5. The colloidal dispersion according to claim 1 where the concentration of silver ions is from 5 ppm to 5,000 ppm.

6. The colloidal dispersion according to claim 1 where the concentration of silver ions is from 100 ppm to 5,000 ppm.

7. The colloidal dispersion according to claim 1 where the dispersion has a pH from 8 to 10.5.

8. The colloidal dispersion according to claim 1 where the concentration of silica in the colloidal dispersion is from 1-25%.

9. A process for making a colloidal dispersion comprising the following steps:
 a) providing a silica sol,
 b) adding a solution of silver nitrate to the silica sol under agitation yielding a stable biocidal colloidal dispersion comprising carrier particles of silica having a particle size from 3 nm to 100 nm to which silver ions have been adsorbed in an amount of 0.0005-5 silver ions per $nm^2$ of silica particle surface, wherein the colloidal dispersion is stable towards gelling and precipitation and has a concentration of silver ions of 5 ppm to 10,000 ppm and the carrier particles and adsorbed silver ions provide biocidal activity.

10. A process for making a colloidal dispersion comprising the following steps:
 a) providing a silica sol,
 b) adding a solution of sodium aluminate to a silica sol without aluminum silicate sites on the sol particles,
 c) adding a solution of silver nitrate to the silica sol under agitation yielding a stable biocidal colloidal dispersion comprising carrier particles of silica having a particle size from 3 nm to 100 nm to which silver ions have been adsorbed in an amount of 0.0005-5 silver ions per $nm^2$ of silica particle surface, wherein the colloidal dispersion is stable towards gelling and precipitation and has a concentration of silver ions of 5 ppm to 10,000 ppm and the carrier particles and adsorbed silver ions provide biocidal activity.

11. A process for making a colloidal dispersion comprising the following steps:
 a) providing a silica sol with aluminosilicate sites on the surface of the sol particles.
 b) adding a solution of silver nitrate to the silica sol under agitation yielding a stable biocidal colloidal dispersion comprising carrier particles of silica having a particle size from 3 nm to 100 nm to which silver ions have been adsorbed in an amount of 0.0005-5 silver ions per $nm^2$ of silica particle surface, wherein the colloidal dispersion is stable towards gelling and precipitation and has a concentration of silver ions of 5 ppm to 10,000 ppm and the carrier particles and adsorbed silver ions provide biocidal activity.

* * * * *